US011447528B2

(12) United States Patent
Flehmig

(10) Patent No.: US 11,447,528 B2
(45) Date of Patent: Sep. 20, 2022

(54) METHOD FOR EXTRACTING HEPATITIS A VIRUS (HAV) ANTIGEN FROM CELL CULTURE

(71) Applicant: Mediagnost Gesellschaft für Forschung und Herstellung von Diagnostika GmbH, Reutlingen (DE)

(72) Inventor: Bertram Flehmig, Tubingen (DE)

(73) Assignee: Mediagnost Gesellschaft für Forschung und Herctellung von Diagnostika GmbH

( * ) Notice: Subject to any disclaimer, the term of this patent is extended or adjusted under 35 U.S.C. 154(b) by 0 days.

(21) Appl. No.: 17/430,474

(22) PCT Filed: Feb. 11, 2020

(86) PCT No.: PCT/EP2020/053376
§ 371 (c)(1),
(2) Date: Aug. 12, 2021

(87) PCT Pub. No.: WO2020/165113
PCT Pub. Date: Aug. 20, 2020

(65) Prior Publication Data
US 2022/0089649 A1 Mar. 24, 2022

(30) Foreign Application Priority Data
Feb. 13, 2019 (EP) .................................... 19156944

(51) Int. Cl.
*C07K 14/005* (2006.01)
*C12N 7/00* (2006.01)
(52) U.S. Cl.
CPC .............. *C07K 14/005* (2013.01); *C12N 7/00* (2013.01); *C12N 2770/32434* (2013.01); *C12N 2770/32451* (2013.01); *C12N 2770/32463* (2013.01)

(58) Field of Classification Search
None
See application file for complete search history.

(56) References Cited

U.S. PATENT DOCUMENTS

| | | | | |
|---|---|---|---|---|
| 5,731,187 | A | 3/1998 | Fanget et al. | |
| 2003/0124511 | A1 | 7/2003 | Tauer et al. | |
| 2004/0152183 | A1 | 8/2004 | O'Riordan et al. | |
| 2005/0003507 | A1 | 1/2005 | Kostel et al. | |
| 2005/0112144 | A1 * | 5/2005 | D'Hondt .................. | A61P 1/16 424/226.1 |
| 2010/0183653 | A1 | 7/2010 | Masignani et al. | |

FOREIGN PATENT DOCUMENTS

| | | | |
|---|---|---|---|
| EP | 0302692 | A2 | 2/1989 |
| EP | 0522291 | A1 | 1/1993 |
| EP | 0583142 | A2 | 2/1994 |
| WO | 9708298 | A1 | 3/1997 |
| WO | 0111065 | A2 | 2/2001 |
| WO | 2004112707 | A2 | 12/2004 |
| WO | 2006085959 | A2 | 8/2006 |

OTHER PUBLICATIONS

Cohen et al., "Attenuation and Cell Culture Adaptation of Hepatitis A Virus (HAV): a Genetic Analysis with HAV cDna", Journal of Virology, Dec. 1989, pp. 5364-5370, vol. 63, No. 12.
Flehmig, "Hepatitis A-Virus in Cell Culture: I. Propagation of Different Hepatitis A-Virus Isolates in a Fetal Rhesus Mondey Kidney Cell Line (Frhk-4)", Medical Microbiology and Immunology, 1980, pp. 239-248, vol. 168.
Flehmig et al., "Hepatitis A Virus in Cell Culture III. Propagation of Hepatitis A Virus in Human Embryo Kidney Cells and Human Embryo Fibroblast Strains", Medical Microbiology and Immunology, 1981, pp. 83-89, vol. 170.
Graff et al., "Nucleotide Sequence of Wild-Type Hepatitis A Virus GBM in Comparison with Two Cell Culture-Adapted Variants", Journal of Virology, Jan. 1994, pp. 548-554, vol. 68, No. 1.
Martin et al., "Hepatitis A Virus: From Discovery to Vaccines", Hepatology, 2006, pp. 164-172, vol. 43, No. 2.
Provost et al., "Propagation of Human Hepatitis A Virus in Cell Culture in Vitro", Proceedings of the Society for Experimental Biology and Medicine, 1979, pp. 213-221, vol. 160.
Provost et al., "Progress Toward a Live, Attenuated Human Hepatitis A Vaccine", Proceedings of the Society for Experimental Biology and Medicine, 1982, pp. 8-14, vol. 170.
Provost et al., "An Inactivated Hepatitis A Viral Vaccine of Cell Culture Origin", Journal of Medical Virology, 1986, pp. 23-31, vol. 19.
Provost et al., "New Findings in Live, Attenuated Hepatitis A Vaccine Development", Journal of Medical Virology, 1986, pp. 165-175, vol. 20.
Vaughan et al., "Hepatitis A Virus: Host Interactions, Molecular Epidemiology and Evolution", Infection, Genetics and Evolution, 2014, pp. 227-243, vol. 21.
Wang et al., "Hepatitis A Virus and the Origins of Picornaviruses", Nature, Jan. 1, 2015, pp. 1-23.
Bishop, et al., "Rapid and Efficient Purification of Hepatitis A Virus from Cell Culture", Journal of Virological Methods, 1994, pp. 203-216, vol. 47.

* cited by examiner

*Primary Examiner* — Nianxiang Zou
(74) *Attorney, Agent, or Firm* — The Webb Law Firm

(57) ABSTRACT

The present invention is directed to a method for extracting hepatitis A virus (HAV) antigen from a cell culture as well as a use of a composition for extracting hepatitis A virus (HAV) antigen from a cell culture.

12 Claims, 2 Drawing Sheets

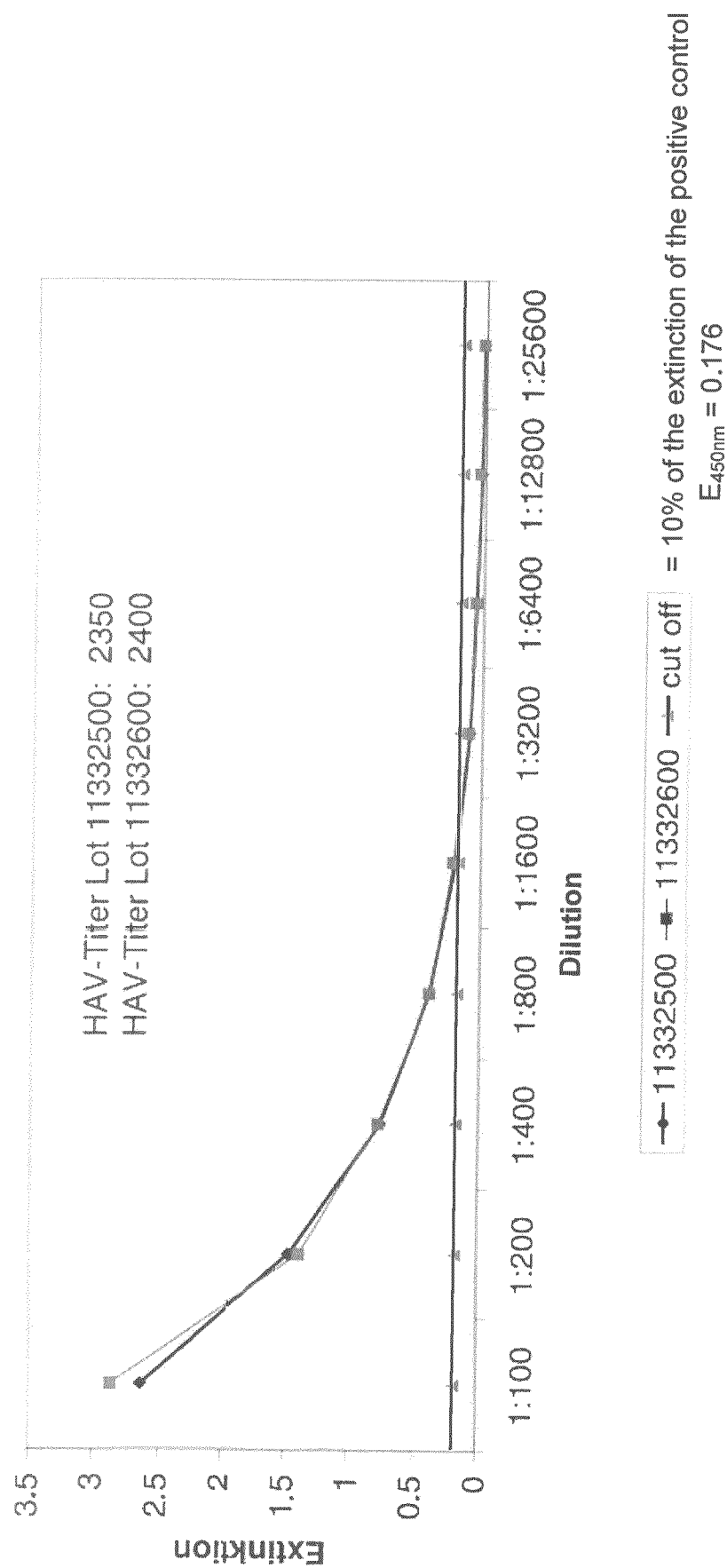

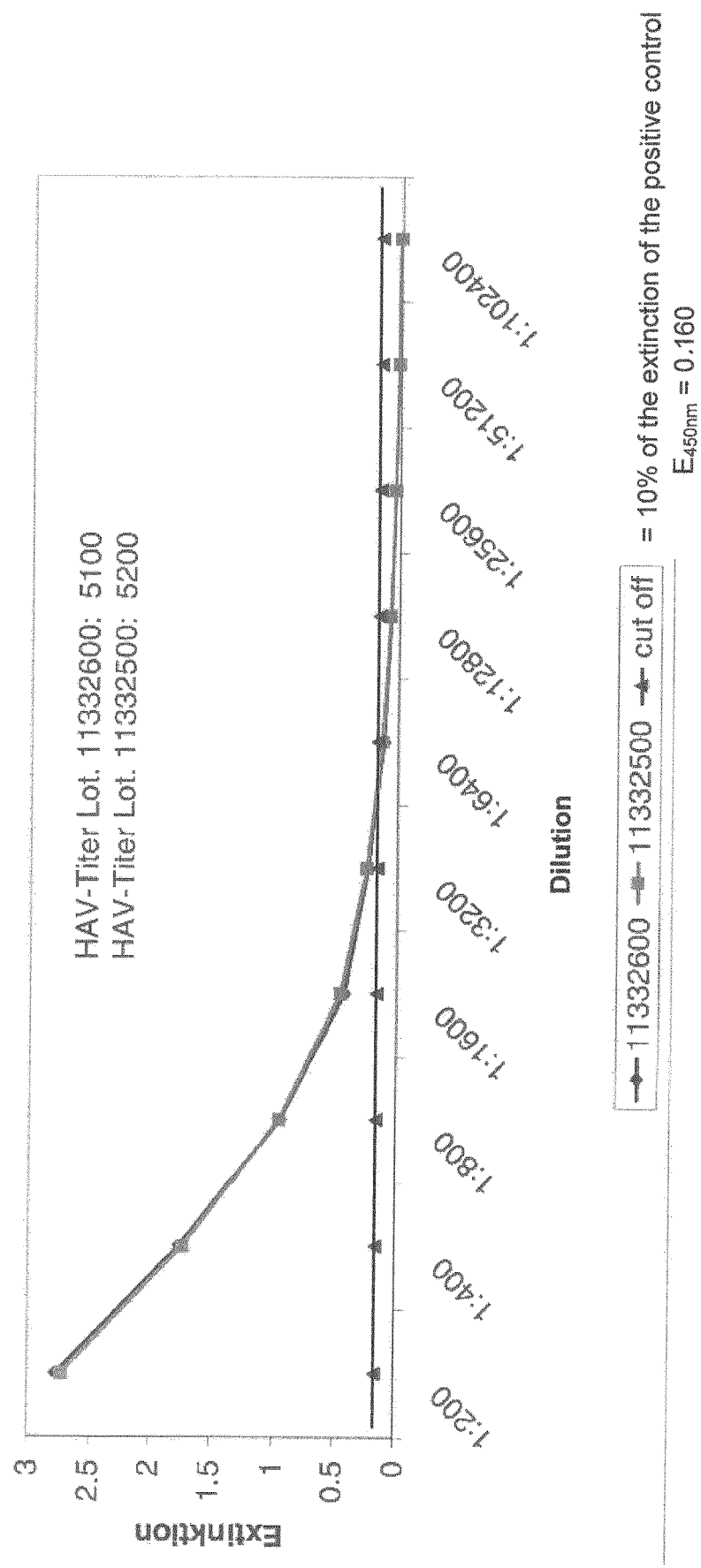
Figure 1 B: HAV extracts prepared as described in example 2

METHOD FOR EXTRACTING HEPATITIS A VIRUS (HAV) ANTIGEN FROM CELL CULTURE

CROSS-REFERENCE TO RELATED APPLICATIONS

This application is the United States national phase of International Application No. PCT/EP2020/053376 filed Feb. 11, 2020, and claims priority to European Patent Application No. 19156944.1 filed Feb. 13, 2019, the disclosures of each of which are hereby incorporated by reference in their entirety.

SUMMARY

The present invention is directed to a method for extracting hepatitis A virus (HAV) antigen from a cell culture as well as a use of a composition for extracting hepatitis A virus (HAV) antigen from a cell culture.

Hepatitis A, which presents a major health problem globally, is caused by hepatitis A virus (HAV).

Hepatitis A virus, whose primary site of replication is the liver, is the most common agent causing acute liver disease worldwide. The incidence of hepatitis A varies greatly from country to country and is associated with socioeconomic factors that impact on the quality of sanitation and access to potable water.

Severity of disease is strongly associated with age, with older children and adults often experiencing symptomatic disease. Hepatitis A virus infection can progress from simple jaundice to acute liver failure (ALF).

Infection with hepatitis A virus usually occurs by the faecal-oral route of transmission and is associated with extensive shedding of the virus in faeces during the 3- to 6-week incubation period and extending into the early days of the illness. Lower amounts of the virus are excreted in the faeces for weeks and months and may be present in the blood also for a long period. This explains the high prevalence of infection in regions where low standards of sanitation promote transmission of hepatitis A virus.

Hepatitis A virus is exceptionally stable at ambient temperatures and at low pH. These features of the virus explain its ability to survive in the environment and to be transmitted by contaminated food and drinking water. Resistance to acid pH and detergents also accounts for its ability to transit through the stomach, and to exit the host via the biliary tract. These are important features that contribute significantly to the pathogenesis of hepatitis A.

Hepatitis A virus has several characteristics that make it unique among the picornaviridae, particularly in terms of its mechanisms of polyprotein processing and virion morphogenesis, and which likely contribute to its pathobiology.

A summary of the origins of hepatitis A virus and picornaviruses can be found in Wang, X. et al. (2015) ("Hepatitis A virus and the origins of picornaviruses", Nature 517 (7532), pages 85 to 88. doi: 10.1038/nature13806).

Hepatitis A virus has a single-stranded (+) RNA genome of 7.5-kilobases (kb) long. The viral genome has a single open reading frame (ORF) encoding a polyprotein of approximately 250 kDa. The nucleic acid sequence of the complete hepatitis A virus genome is, for example, available under the GenBank accession number M14707.1.

The viral proteins are translated directly from the messenger-sense genomic RNA, which is delivered to the cytoplasm after uncoating of the viral particle.

Hepatitis A virus gene expression and protein assembly require maturation of individual proteins by co- and post-translational proteolysis from the polyprotein, which consists of 3 major regions, known as P1, P2 and P3. The P1 region is processed into three structural proteins of the viral capsid, VP1, VP2, VP3, and the viral capsid protein, which is designated VP4 and which is essential for virion formation but not present in the mature virus particles.

The structural proteins are cleaved by the viral protease 3C, which is encoded in the P3 region. Nonstructural proteins are processed from the P2 and P3 regions, and are required for RNA synthesis and virion assembly. The P3 segment contains the 3A, 3B, 3C and 3D proteins.

A summary of the molecular characteristics of hepatitis A virus can be found in Vaughan, G. et al. (2014) ("Hepatitis A virus: host interactions, molecular epidemiology and evolution", Infect. Genet. Evol. 21, pages 227 to 243, doi: 10.1016/j.meegid.2013.10.023).

Hepatitis A virus has been shown to possess a main conserved antigenic neutralization site and, as a result, all isolates from different parts of the world belong to a single serotype.

Experiments with hepatitis A virus (HAV) immune-escape mutants, representing antigenic variants and exhibiting variable degrees of resistance to different monoclonal antibodies (MAbs), suggest that the existence of severe structural constraints in the HAV capsid that prevent a more extensive genetic variation necessary for the emergence of a new serotype since all observed immune-escape variants shared substitutions along the VP3 protein.

The adaptive immune response to hepatitis A virus is robust and extremely effective in eliminating the virus. Neutralizing antibodies to the virus (anti-HAV) generally appear in the serum concurrent with the earliest evidence of serum aminotransferase elevation and hepatocellular injury. Anti-HAV IgG persists for life and confers protection against reinfection, at least against a second illness.

In the past in industrialized countries, hepatitis A vaccination has been recommended for persons at increased risk of acquiring hepatitis A, including travellers to regions of high hepatitis A endemicity, users of illicit drugs, homosexually active men, and patients with clotting factor disorders who receive factor concentrates.

Immunization also has been recommended for persons who are at increased risk of developing fulminant disease should they become infected with hepatitis A virus.

Live, attenuated HAV vaccines have been developed using viruses that have been adapted to growth in cell culture. However, vaccine candidates were poorly immunogenic. Whereas an attenuated vaccine might have some advantages, inactivated vaccines work well.

Inactivated HAV vaccines contain viral particles that are produced in cell culture, purified, inactivated with formalin, and adsorbed to an adjuvant, such as aluminum hydroxide.

Inactivated HAV vaccines are highly immunogenic and protect against both infection and disease. This protection is likely primarily antibody based, and is broadly directed against all strains of hepatitis A virus, consistent with the identification of a single serotype of hepatitis A virus among human strains.

Although efficacious vaccines containing formalin-inactivated virus produced in cell culture have been licensed in multiple countries, their use has been limited by cost considerations, which inter alia result from difficult culture conditions.

Hepatitis A virus has been adapted to replicate in many types of cultured mammalian cells, including cells of nonhepatic or non-primate origins. Several features of its replication cycle distinguish it from poliovirus and many other well studied picornaviruses, including its slow and protracted time course, low virus yields, and a propensity to establish persistent infections in cell culture.

The growth of wild-type virus is generally poor in cultured cells, and the virus preferably undergoes a process of adaptation before becoming capable of efficient replication.

A few highly cell culture-adapted, rapidly replicating strains of hepatitis A virus have been isolated. These viruses are cytopathic and appear to cause cell death by inducing apoptosis. However, in most HAV-infected cells, both in cell culture and probably also in vivo, there is no cytopathic effect. The virus apparently down-regulates its replication in cells commonly used for its propagation, such as foetal rhesus monkey kidney (FRhK-4) cells or human lung fibroblast cell lines, such as MRC-5.

The relatively high costs of a vaccine relate in part to difficulties inherent in propagating hepatitis A virus in cell culture, but also to the current limited scale of manufacture.

A summary of the development of HAV vaccines can be found in Martin, A. and Lemon, S. M. (2006) ("Hepatitis A virus: From discovery to vaccines", Hepatology 43(2), pages 164 to 172, https://doi.org/10.1002/hep.21052).

A process for purification of hepatitis A virions is described in EP 0 302 692 A2.

EP 0 522 291 A1 discloses a process for purifying hepatitis A virus (HAV), and vaccine compositions containing hepatitis a virus.

U.S. Pat. No. 5,731,187 A is directed to a process for preparing hepatitis A virus (HAV) antigens and vaccines.

The methods known in the art rely on the growth of HAV-infected cells on a culture substrate and scraping of cells or trypsinization of cells is a requirement for harvesting a suspension of HAV-infected cells. HAV-infected cells are normally collected by means of centrifugation.

Alternatively, suspension cell cultures can be used and HAV-infected cells are harvested by centrifugation from the cell culture medium.

In all cases, HAV-infected cells are lysed by any one or more of a variety of techniques, including but not limited to exposure to hypotonic buffer, vortexing, freeze-thaw cycling, and sonication, in order to releases sufficient amounts of HAV antigen from the harvested cells and cell debris is removed from the lysate by means of centrifugation.

The supernatant is then subjected to an extraction procedure. Such extraction removes, among other contaminants, lipid and lipid-like substances. Suitable extraction procedures include organic extraction by means of an organic solvent, chromatography, gel filtration and/or centrifugation.

However, the methods known in the art are relatively time-consuming and do have a significant loss in the yield of HAV-antigen.

Therefore, it is an object of the present invention to provide a method for extracting hepatitis A virus (HAV) antigen from a cell culture which provides for an increased amount of HAV-antigen and which also is feasible for large scale antigen production, preferably, without reducing antigenicity of HAV-antigen obtained.

BRIEF DESCRIPTION OF THE DRAWINGS

FIG. 1A depicts HAV extracts prepared as described in example 3.

FIG. 1B depicts HAV extracts prepared as described in example 2.

DETAILED DESCRIPTION

The object of the present invention is solved by the provision of the method of claim 1 for extracting hepatitis A virus (HAV) antigen from a cell culture, the method comprises the steps of:

a) providing at least one mammalian cell expressing a nucleic acid coding for hepatitis A virus (HAV) antigen,
b) lysing the at least one mammalian cell expressing the nucleic acid coding for hepatitis A virus (HAV) antigen by contacting the cells with at least one protease and at least one surfactant, and
c) collecting a lysate comprising hepatitis A virus (HAV) antigen.

Preferred embodiments of the method of the present invention are disclosed in dependant claims 2 to 10.

The object of the present invention is further solved by the provision of the use according to claim 11 of a composition for extracting hepatitis A virus (HAV) antigen from a cell culture, the composition comprises at least one protease and at least one surfactant.

Preferred embodiments of the use of the present invention are disclosed in dependant claims 12 to 14.

In the method of the present invention for extracting a HAV-antigen from a cell culture comprising at least one mammalian cell expressing a nucleic acid coding for HAV-antigen, the at least one mammalian cell is lysed by contacting the at least one mammalian cell with at least one protease and at least one surfactant, preferably for at least 10 hours, preferably for at least 12 hours, preferably for a period of from 10 hours to 36 hours, further preferably for a period of from 12 hours to 24 hours, preferably at a temperature of at least 20° C., preferably at a temperature of at least 25° C., preferably at a temperature of at least 37° C., further preferably at a temperature in the range of from 20° C. to 38° C., further preferably at a temperature in the range of from 25° C. to 37° C.

The inventors of the present invention found out, that HAV-antigen can efficiently be released from at least one mammalian cell expressing a nucleic acid coding for HAV-antigen by lysing the at least one mammalian cell with a combination of at least one protease and at least one surfactant for a sufficient period of time, preferably for at least 10 hours, further preferably for at least 12 hours, preferably for a period of from 10 hours to 36 hours, further preferably for a period of from 12 hours to 24 hours, preferably at a temperature of at least 20° C., preferably at a temperature of at least 25° C., preferably at a temperature of at least 37° C., further preferably at a temperature in the range of from 20° C. to 38° C., further preferably at a temperature in the range of from 25° C. to 37° C., further preferably without the necessity of precipitating cellular debris by means, for example, of sedimentation under gravity or centrifugation after lysis of the disrupted host cell.

The combined application of at least one protease and at least one surfactant for a sufficient period of time, preferably for at least 10 hours, preferably for at least 12 hours, preferably for a period of from 10 hours to 36 hours, further preferably for a period of from 12 hours to 24 hours, preferably at a temperature of at least 20° C., preferably at a temperature of at least 25° C., preferably at a temperature of at least 37° C., further preferably at a temperature in the range of from 20° C. to 38° C., further preferably at a temperature in the range of from 25° C. to 37° C., provides for an efficient disruption of an HAV-antigen expressing host cell by which preferably any HAV-antigen from the host cell is released into the lysate obtained in step b) of the method of the present invention.

A "combined application" means according to the invention that the at least one protease and the at least one surfactant can act substantially simultaneously on the HAV-expressing, preferably HAV-infected, mammalian cells. That is to say at least one protease and/or the at least one surfactant can also be added one after another to the HAV-expressing, preferably HAV-infected, mammalian cells. It is only important that at least one protease and the at least one surfactant act on together for a sufficient period of time during lysis of the HAV-expressing, preferably HAV-infected, mammalian cells.

As a result, a much higher amount of HAV-antigen is obtained by the method of the present invention.

According to the present invention the term "hepatitis A virus antigen" or "HAV-antigen" refers to at least the portion of the hepatitis A virus capsid protein, which provides immunogenicity. Preferably said HAV-antigen comprises at least one of the mature VP1 capsid protein of hepatitis A virus, the mature VP2 capsid protein of hepatitis A virus, the mature VP3 capsid protein of hepatitis A virus, and/or mixtures thereof, preferably at least one of the mature VP1 capsid protein of hepatitis A virus and/or the mature VP3 capsid protein of hepatitis A virus.

The amino acid sequence of the hepatitis A virus polyprotein is available under the UniProt accession number Q67825, version 106.

The mature VP1 capsid protein, the mature VP2 capsid protein and the mature VP3 capsid protein of hepatitis A virus are preferably generated from the HAV-polyprotein by enzymatic cleavage by a protease.

The nucleotide sequence of hepatitis A virus, synonymously designated as hepatovirus A, is known and is, for example, disclosed in Graff, J. et al. (1994) ("Nucleotide sequence of wild-type hepatitis A virus GBM in comparison with two cell culture-adapted variants". J. Virol. 68(1), page 548 to 554), the disclosure of which is incorporated herewith by reference. The respective nucleic acid sequences are, for example, available under the GenBank accession numbers X75214.1, X75215.1 and X75216.1.

The term "nucleic acid coding for hepatitis A virus (HAV)" is also meant to comprise mutants and/or functional equivalents of HAV. A "functional equivalent" means a nucleic acid sequence coding for a truncated or mutated HAV-antigen, eliciting substantially the same immune reaction after vaccination or application to a human being, compared to a vaccination or application of the wild-type HAV.

Preferably, the coding sequence of the HAV expressing mammalian cell comprises the nucleic acid sequence encoding for the P1 region of the polyprotein of the wild type hepatitis A virus, strain GBM, which preferably corresponds to nucleotide position 688 to 3060 of the nucleic acid sequence available under the GenBank accession number X75215.1.

According to the method of the present invention HAV-antigen is extracted from a cell culture comprising at least one, preferably HAV infected, mammalian cell expressing a nucleic acid coding for the HAV-antigen.

Preferably, the cell culture comprising the at least one, preferably HAV infected, mammalian cell expressing a nucleic acid coding for the HAV-antigen is an adherent cell culture or as suspension cell culture, preferably an adherent cell culture.

The majority of the cells derived from mammalians, with the exception of hematopoietic cell lines and a few others, are preferably anchorage-dependent cells and are cultured on a suitable substrate that is further preferably specifically treated by methods known in the art to allow cell adhesion and spreading of cells.

However, many cell lines can also be adapted for suspension culture.

Cells that are cultured in suspension can be maintained in culture flasks that are not tissue-culture treated, but as the culture volume to surface area is increased beyond which adequate gas exchange is hindered, the medium requires agitation, for example by means of a magnetic stirrer or rotating spinner flasks.

Preferably, in step a) said at least one, preferably HAV infected, mammalian cell expressing HAV-antigen is provided as adherent cell culture, in which the least one, preferably HAV infected, mammalian cell expressing a nucleic acid coding for HAV-antigen is grown as a monolayer in a suitable growth medium under conditions known in the art.

The at least one, preferably HAV infected, mammalian cell expressing HAV-antigen provided in step a) of the method of the present invention can be obtained by methods known in the art, for example by infecting at least one mammalian cell with a sufficient amount of a hepatitis A virus.

HAV-infected cells are grown and harvested by any one or more of a variety of conventional cell culture techniques.

Preferably, hepatitis A virus used for obtaining the at least one mammalian cell expressing the HAV-antigen is adapted to growth in cell culture, preferably to the cell line used for expressing the HAV-antigen.

Hepatitis A virus has been adapted to replicate in many types of preferably cultured cells by method known in the art as, for example, as disclosed in Graff, J. et al. (1994), Cohen, J. I. (1989), ("Attenuation and cell culture adaptation of hepatitis A virus (HAV): a genetic analysis with HAV cDNA", J. Virol. 63(12), pages 5364 to 5370), or Flehmig, B. et al. (1981) ("Hepatitis A virus in cell culture. III. Propagation of hepatitis A virus in human embryo kidney cells and human embryo fibroblast strains", Med. Microbiol. Immunol. 170(2), pages 83 to 89).

Growth conditions, including the selection of media, depend on the requirements of the respective cell line employed and are known to the skilled person.

Further preferably, culture medium is removed before contacting the at least one mammalian cell expressing the nucleic acid coding for hepatitis A virus (HAV) antigen with at least one protease and at least one surfactant in step b).

Suitable cell lines include known mammalian cell lines, for example, human embryo kidney cells, foetal rhesus monkey kidney (FRhK-4) cells, human lung fibroblast cell line, preferably MRC-5, Buffalo Green Monkey Kidney (BGMK) cells from African green monkey kidney and mixtures thereof.

For example, MRC-5 cells require attachment to a substratum, so that in step b) of the method of the present invention HAV-antigen can efficiently be extracted from MRC-5 cells expressing the HAV-antigen by contacting the cells, which are attached to a cell culture support, with the combination of at least one protease and at least one surfactant.

According to the present invention a composition comprising at least one protease and at least one surfactant is used for extracting HAV-antigen from a cell culture, preferably by simultaneous, sequential or combined application of said at least one protease and said at least one detergent.

Preferably, said at least one protease and said at least one detergent are applied to the at least one cell in form of a, preferably liquid, lysing composition.

Preferably, by contacting the at least one, preferably HAV infected, mammalian cell in which a nucleic acid coding for HAV-antigen is expressed with the combination of at least one protease and at least one surfactant in step b) of the method of the present invention under the above-indicated conditions a lysate is provided in which a significant amount of HAV-antigen is comprised.

Preferably, said at least one surfactant, which is used in combination with said at least one protease in the method of the present invention, is selected from the group consisting of anionic surfactants, cationic surfactants, zwitterionic surfactants, non-ionic surfactants and mixtures thereof.

Further preferably, said at least one surfactant is a non-ionic surfactant selected from the group consisting of alkoxylated linear alcohols, alkoxylated alkyl phenols, alkoxylated thiols, fatty acid alkoxylates, alkoxylated amines and/or fatty acid amides, copolymers of ethylene oxide and propylene oxide, fatty acid esters of polyhydroxy compounds, alkyl ethers of polyhydroxy compounds, amine oxides, sulfoxides, phosphine oxides, and mixtures thereof.

Further preferably, said at least one surfactant is selected from the group consisting of fatty acid esters of polyhydroxy compounds, alkyl ethers of polyhydroxy compounds and mixtures thereof, such as sorbitan fatty acid esters, alkoxylated sorbitan fatty acid esters, and mixtures thereof, which for example are commercy available under the trademark Tween® by Croda International PLC (Snaith, UK).

Suitable non-ionic surfactants are, for example, polyoxyethylene (20) sorbitan monolaurate (Polysorbate 20, Tween® 20), polyoxyethylene (4) sorbitan monolaurate (Polysorbate 21, Tween® 21), polyoxyethylene (20)-sorbitan monopalmitate (Polysorbate 40, Tween® 40), polyoxyethylene (20)-sorbitan monostearate (Polysorbate 60, Tween® 60), polyoxyethylene (4)-sorbitan monostearate (Polysorbate 61, Tween® 61), polyoxyethylene (20)-sorbitan tristearate (Polysorbate 65, Tween® 65), polyoxyethylene (20)-sorbitan monooleate (Polysorbate 80, Tween® 80), polyoxyethylene (5)-sorbitan monooleate (Polysorbate 81, Tween® 81), polyoxyethylene (20)-sorbitan trioleate (Polysorbate 85, Tween® 85), polyoxyethylene (20)-sorbitan monoisostearate (Polysorbate 120), or mixtures thereof, preferably polyoxyethylene (20) sorbitan monolaurate.

Preferably, said at least one surfactant is used in a concentration of at least 0.05 vol.-% per mL, preferably of at least 0.1 vol.-% per mL, preferably of from 0.05 vol.-% per mL to 5.0 vol.-% per mL, further preferably of from 0.1 vol.-% per mL to 1.5 vol.-% per mL, each based on the volume of the at least one surfactant per mL of total volume of the lysing composition.

Preferably, said at least one protease, which is used in combination with said at least one surfactant in the method of the present invention, is selected from the group consisting of serine proteases, cysteine proteases, threonine proteases, aspartic proteases, glutamic proteases, metalloproteases, asparagine peptide lyases, and mixtures thereof.

Further preferably, said at least one protease is selected from the group consisting of trypsin, chymotrypsin, papain, and mixtures thereof.

Preferably, said at least one protease is used in a concentration of at least at 0.05 vol.-% per mL, preferably of at least 0.1 wt.-% per mL, preferably of at least 0.5 wt.-% per mL, further preferably of from 0.05 wt.-% per mL to 5.0 wt.-%, further preferably of from 0.1 vol.-% per mL to 1.5 vol.-% per mL, further preferably of from 0.5 vol.-% per mL to 1.0 vol.-% per mL, each based on the dry weight of the at least one protease per total volume of the lysing composition.

Further preferably, said lysing composition comprises at least Tween 20 in a concentration of from 0.1 vol.-% per mL to 1.5 vol.-% per mL, further preferably of from 0.5 vol.-% per mL to 1.0 vol.-% per mL, each based on the volume of Tween 20 per mL of total volume of the lysing composition, and at least Trypsin in a concentration of from 0.1 vol.-% per mL to 1.5 vol.-% per mL, further preferably of from 0.5 vol.-% per mL to 1.0 vol.-% per mL, each based on the dry weight of Trypsin per total volume of the lysing composition.

Preferably, the activity of said protease can be controlled by addition of at least one chelating agent, such as ethylenediaminetetraacetic acid (EDTA).

Further preferably, in step b) of the method of the present invention said lysing of the at least one vertebrate cell expressing the HAV-antigen is achieved by contacting the cells with at least one protease and at least one surfactant in the presence of at least one chelating agent.

Preferably, the lysis of the cells is effected only by the combined action of at least one protease and at least one detergent, preferably without any further action of, for example, ultrasonic lysis or mechanical lysis, such as French press cell lysis.

Preferably, the lysate obtained in step b) of the method of the present invention comprising HAV-antigen is collected in step c) of the method of the present invention and can be stored or used directly for subsequent applications.

Additional processing steps of conventional and well known character may be applied to prepare purified HAV-antigen.

Further preferably, the HAV-antigen comprised in the lysate obtained in step c) can be concentrated in step d), preferably by means of filtration, chromatography, dialysis, electrophoresis, centrifugation, or a combination thereof.

A further purification step is the use of at least one polar liquid such as chloroform for an extraction of the lipoproteins from the lysate.

The lysate and the at least one polar liquid such as chloroform, preferably 4 parts lysate, 1 part polar liquid such as chloroform, are mixed together and shaken strongly, thereafter the lysate and the polar liquid such as chloroform are separated, for example by centrifugation, and the lysate is used for further purposes.

For example, treatment with formalin, sterile filtration and adsorption to carriers or adjuvants are the typical basic steps for preparing a formalin-inactivated vaccine, as described, for example, in Provost, P. J. et al. (1979) ("Propagation of human hepatitis A virus in cell culture in vitro"; Proc. Soc. Exp. Biol. Med. 160 (2), pages 213 to 221) and Provost, P. J. et al. (1986) ("An inactivated hepatitis A viral vaccine of cell culture origin"; J. Med. Virol. 19 (1), pages 23 to 31).

Said HAV-antigen can be inactivated, for example, by heat, pH changes, treatment with organic solvents, ultraviolet irradiation, and/or exposure to an aldehyde, such as formaldehyde, and/or an aldehyde-releasing agent, such as an formaldehyde releasing agent.

Further preferably, said HAV-antigen obtained by the method of the present invention is inactivated by contacting said HAV-antigen with at least one aldehyde and/or aldehyde releasing agent, preferably formaldehyde and/or formaldehyde releasing agent, for a sufficient period of time, preferably at least 7 days, preferably at least 9 days, further preferably at least 11 days, at a temperature of at least 20° C. preferably at a temperature of 37° C., further preferably at least 21 days.

The method of the present invention can be applied to any known hepatitis A virus (HAV) strain, whether or not attenuated. Attenuated strains may be isolated by serial passage through cells, animals, or by other methods. See, for example, Provost, P: J. et al. (1982) ("Progress toward a live, attenuated human hepatitis A vaccine"; Proc. Soc. Exp. Biol. Med. 170 (1), pages 8 to 14) and Provost, P. J. et al. (1986) ("New findings in live, attenuated hepatitis A vaccine development"; J. Med. Virol. 20 (2), pages 165 to 175), for details on attenuation.

The method of the present invention is readily and easily adaptable to attenuated or unattenuated strains of hepatitis A virus.

The HAV-antigen obtained by the method of the present invention can be used for generating a hepatitis A virus antibody or an inactivated hepatitis A vaccine.

EXAMPLES

The following Example is given for illustrative purpose only. The invention is not to be construed to be limited to the following Example.

Example 1: Generation of HAV Expressing Cells

MRC-5 human diploid fibroblast cells (Lot 1) or foetal rhesus monkey kidney (Frhk-4) cells (Lot 2) were each infected with hepatitis A virus (GBM strain) by the method described in Flehmig, B. (1980) ("Hepatitis A-virus in cell culture: I. propagation of different hepatitis A-virus isolates in a foetal rhesus monkey kidney cell line (Frhk-4)"; Med. Microbiol. Immunol. 168(4), pages 239 to 248).

After infection cells were passaged 2 times and split in two separate vessels A and B, each having an identical number of cells after an incubation of 3 weeks.

From each vessel (1A and 1B) HAV-antigen was extracted by application of either a conventional extraction method or by the method of the present invention.

Example 2: Extraction of HAV-Antigen by the Method of the Present Invention

Cell culture medium was removed by aspiration prior to application of a prewarmed (37° C.) solution having the following composition:
  0.5 wt.-% Trypsin (Sigma Aldrich Chemie GmbH, Munich, De)
  0.1 vol.-% Tween-20
  in Hank's Balanced Salt Solution, final pH: 7.4 to 7.6
  in an amount sufficient to cover the cell layer (approximately 0.5 mL per 10 cm²).

Cells were incubated over night at 37° C.

At the next day the lysate was collected and the amount of HAV-antigen was determined by the method described in Example 4.

Comparative Example 3: Extraction of HAV-Antigen by a Conventional Extraction Method Cell culture medium was removed by aspiration prior to application of a prewarmed (37° C.) solution having the following composition:
  0.5 wt.-% Trypsin (Sigma Aldrich Chemie Gmbh, Munich, DE)
  in Hank's Balanced Salt Solution, final pH: 7.4 to 7.6
  in an amount sufficient to cover the cell layer (approximately 0.5 mL per 10 cm²).

Cells were incubated for 5 minutes at 37° C. Trypsin was inactivated by adding a sufficient amount of foetal calf serum, preferably 1% or more.

Trypsinated cells were harvested by centrifugation and the supernatant was decarded. The resulting cell pellet was frozen over night at a temperature of from −20° C. to −70° C.

At the next day the frozen cell pellet was thawed at room temperature and subjected to mechanical disruption using an Ultra-Turrax dispersing instrument (IKA-Werke GmbH & CO. KG, Staufen, DE) for approximately 5 min.

After mechanical disruption the suspension was centrifuged again and the supernatant was removed and collected.

The amount of HAV-antigen in the supernatant was determined by the method described in Example 4.

Example 4: Determination of HAV-Antigen

Determination of HAV-antigen was performed using the HAV-Antigen enzyme-linked immunosorbent assay (ELISA) kit, product number E12, commercially available from Mediagnost Gesellschaft für Forschung and Herstellung von Diagnostika GmbH according to the manufacturer's instruction.

Briefly, 50 µl aliquots of each cell lysate obtained in Example 2 and Comparative Example 3 were pipetted into wells of a microtiter plate included with the ELISA kit.

Wells were pre-coated with an antibody directed against the HAV antigen. The HAV antigen present in the respective cell lysate binds to the fixed antibody and after an incubation period of two hours at 37° C. the microtiter plate was washed thoroughly with wash buffer supplied with the kit.

Bound HAV antigen was subsequently identified by addition of a peroxidase conjugated mouse monoclonal anti-HAV IgG antibody, which was also supplied with the kit, and incubation for another two hours at 37° C.

Excess peroxidase conjugated antibody was removed by washing with wash buffer. Subsequently, substrate solution, containing 3,3',5,5'-tetramethylbenzidine (TMB), was added for ELISA development.

After 30 minutes incubation at room temperature the reaction was terminated by adding stop solution. The blue colour in the wells changed to yellow and absorbance was measured in a microplate reader at a wavelength of 450 nm.

The intensity of the colour indicated the concentration of bound HAV antigen.

The titer is defined as the dilution of the HAV-antigen preparation having an extinction at the above indicated wavelength of 10% of the positive control. The positive control in FIG. 1A was 1.76 and 10% of this value is 0.176%. The positive control in FIG. 1B was 1.6 and 10% of this value is 0.160. Titer determination was performed with two different lots from HAV extracts prepared as described in Example 3 and HAV extracts prepared as described in Example 2.

As can be seen in FIG. 1B, the titers of the extracts prepared as described in Example 2 are substantially higher, nearly the double, compared to the extracts prepared as described in Example 3, seen in FIG. 1A.

With two other samples having a higher HAV-Ag content titer values are achieved as can be seen in Table 1. Also within these samples extractions by Example 2 reached much higher titers compared to Example 3.

The determined HAV-antigen titers of these different lots of each vessel are summarized in Table 1 below.

TABLE 1

Determined HAV-antigen titers

|  | Lot 1 | Lot 2 |
|---|---|---|
| Example 2 | 1:21000 | 1:23000 |
| Comp. Example 3 | 1:15800 | 1:14900 |

The invention claimed is:

1. A method for extracting hepatitis A virus (HAV) antigen from a cell culture, the method comprising the steps of:
   a) providing at least one mammalian cell expressing a nucleic acid coding for a hepatitis A virus (HAV) antigen,
   b) lysing the at least one mammalian cell expressing the nucleic acid coding for said HAV antigen by contacting the cells, which are attached to a cell culture support, with at least one protease and at least one surfactant so that the at least one protease and the at least one surfactant act on the at least one mammalian cell together for a sufficient period of time during lysing, and
   c) collecting a lysate comprising said HAV antigen,
   wherein said HAV antigen comprises at least one of a mature VP1 capsid protein of hepatitis A virus, a mature VP2 capsid protein of hepatitis A virus, a mature VP3 capsid protein of hepatitis A virus, or mixtures thereof.

2. The method according to claim 1, wherein said at least one surfactant is selected from the group consisting of anionic surfactants, cationic surfactants, zwitterionic surfactants, non-ionic surfactants, and mixtures thereof.

3. The method according to claim 1, wherein said at least one surfactant is a non-ionic surfactant selected from the group consisting of alkoxylated linear alcohols, alkoxylated alkyl phenols, alkoxylated thiols, fatty acid alkoxylates, alkoxylated amines or fatty acid amides, copolymers of ethylene oxide and propylene oxide, fatty acid esters of polyhydroxy compounds, alkyl ethers of polyhydroxy compounds, amine oxides, sulfoxides, phosphine oxides, and mixtures thereof.

4. The method according to claim 1, wherein said at least one surfactant is selected from the group consisting of sorbitan fatty acid esters, alkoxylated sorbitan fatty acid esters, and mixtures thereof.

5. The method according to claim 1, wherein said at least one protease is selected from the group consisting of trypsin, chymotrypsin, papain, and mixtures thereof.

6. The method according to claim 1, wherein in step b) said lysing of the at least one mammalian cell expressing the nucleic acid coding for said HAV antigen comprises contacting the cells with at least one protease and at least one surfactant in the presence of at least one chelating agent.

7. The method according to claim 1, further comprising the step of:
   concentrating the HAV antigen comprised in the lysate of step c).

8. The method according to claim 1, further comprising the step of:
   inactivating said HAV antigen by contacting said HAV antigen with at least one aldehyde or aldehyde releasing agent.

9. The method according to claim 1, wherein said HAV antigen comprises at least one of the mature VP1 capsid protein of hepatitis A virus or the mature VP3 capsid protein of hepatitis A virus.

10. The method according to claim 7, wherein concentrating the HAV antigen comprised in the lysate of step c) comprises filtration, chromatography, dialysis, electrophoresis, centrifugation, or a combination thereof.

11. The method according to claim 8, wherein the at least one aldehyde or aldehyde releasing agent is formaldehyde or formaldehyde releasing agent.

12. The method according to claim 1, wherein lysing is performed without subjecting the at least one mammalian cell to a freeze-thaw cycle.

* * * * *

UNITED STATES PATENT AND TRADEMARK OFFICE
CERTIFICATE OF CORRECTION

| | | |
|---|---|---|
| PATENT NO. | : 11,447,528 B2 | Page 1 of 1 |
| APPLICATION NO. | : 17/430474 | |
| DATED | : September 20, 2022 | |
| INVENTOR(S) | : Bertram Flehmig | |

It is certified that error appears in the above-identified patent and that said Letters Patent is hereby corrected as shown below:

On the Title Page

Column 1, Item (73) Assignee, Line 2, delete "Herctellung" and insert -- Herstellung --

Column 1, Item (73) Assignee, Line 3, after "GmbH" insert -- Reutlingen (DE) --

Column 2, Item (56) Other Publications, Line 5, delete "Mondey" and insert -- Monkey --

Signed and Sealed this
Twenty-seventh Day of December, 2022

*Katherine Kelly Vidal*

Katherine Kelly Vidal
*Director of the United States Patent and Trademark Office*